United States Patent [19]

Goering et al.

[11] Patent Number: 4,804,545

[45] Date of Patent: Feb. 14, 1989

[54] PRODUCTION OF BETA-GLUCAN, BRAN, PROTEIN, OIL AND MALTOSE SYRUP FROM WAXY BARLEY

[75] Inventors: Kenneth J. Goering; Robert F. Eslick, both of Bozeman, Mont.

[73] Assignee: Barco, Inc., Bozeman, Mont.

[21] Appl. No.: 150,434

[22] Filed: Jan. 28, 1988

Related U.S. Application Data

[63] Continuation of Ser. No. 914,877, Oct. 3, 1986, abandoned, which is a continuation of Ser. No. 639,345, Aug. 10, 1984, abandoned.

[51] Int. Cl.$^4$ .......................... A23L 1/10; A23J 1/12; C12P 19/22; C12P 19/14
[52] U.S. Cl. ........................................ 426/28; 426/44; 426/52; 426/430; 426/436; 435/95; 435/99
[58] Field of Search ...................... 426/11, 28, 29, 44, 426/52, 430, 436; 435/99, 95

[56] References Cited

U.S. PATENT DOCUMENTS

| | | | |
|---|---|---|---|
| 3,576,645 | 4/1971 | Rozsz | 426/29 X |
| 4,042,414 | 8/1977 | Goering et al. | 127/32 |
| 4,069,103 | 1/1978 | Muller | 426/53 X |
| 4,116,770 | 9/1978 | Goering et al. | 127/32 |
| 4,311,714 | 1/1982 | Goering et al. | 426/52 X |
| 4,428,967 | 1/1984 | Goering et al. | 426/52 X |
| 4,448,790 | 5/1984 | Sarkki et al. | 435/99 X |

OTHER PUBLICATIONS

Gjertsen, P., A.S.B.C. Proceedings, 1982, pp. 113–120.

*Primary Examiner*—David M. Naff
*Attorney, Agent, or Firm*—Lowe, Price, LeBlanc, Becker & Shur

[57] ABSTRACT

Waxy barley grain of reduced particle size is heated to inactivate natural enzymes to obtain an enzyme inactivated meal, and beta-glucans are extracted from the meal with water. Preferably, inactivation of enzymes is by heating at about 90°–115° C. for about 1 to 2 hours. Solids obtained by separation during extraction are treated with alpha-amylase, beta-amylase and beta-glucanase to obtain starch conversion. Barley oil, high protein concentrate and maltose syrup are recovered.

17 Claims, 1 Drawing Sheet

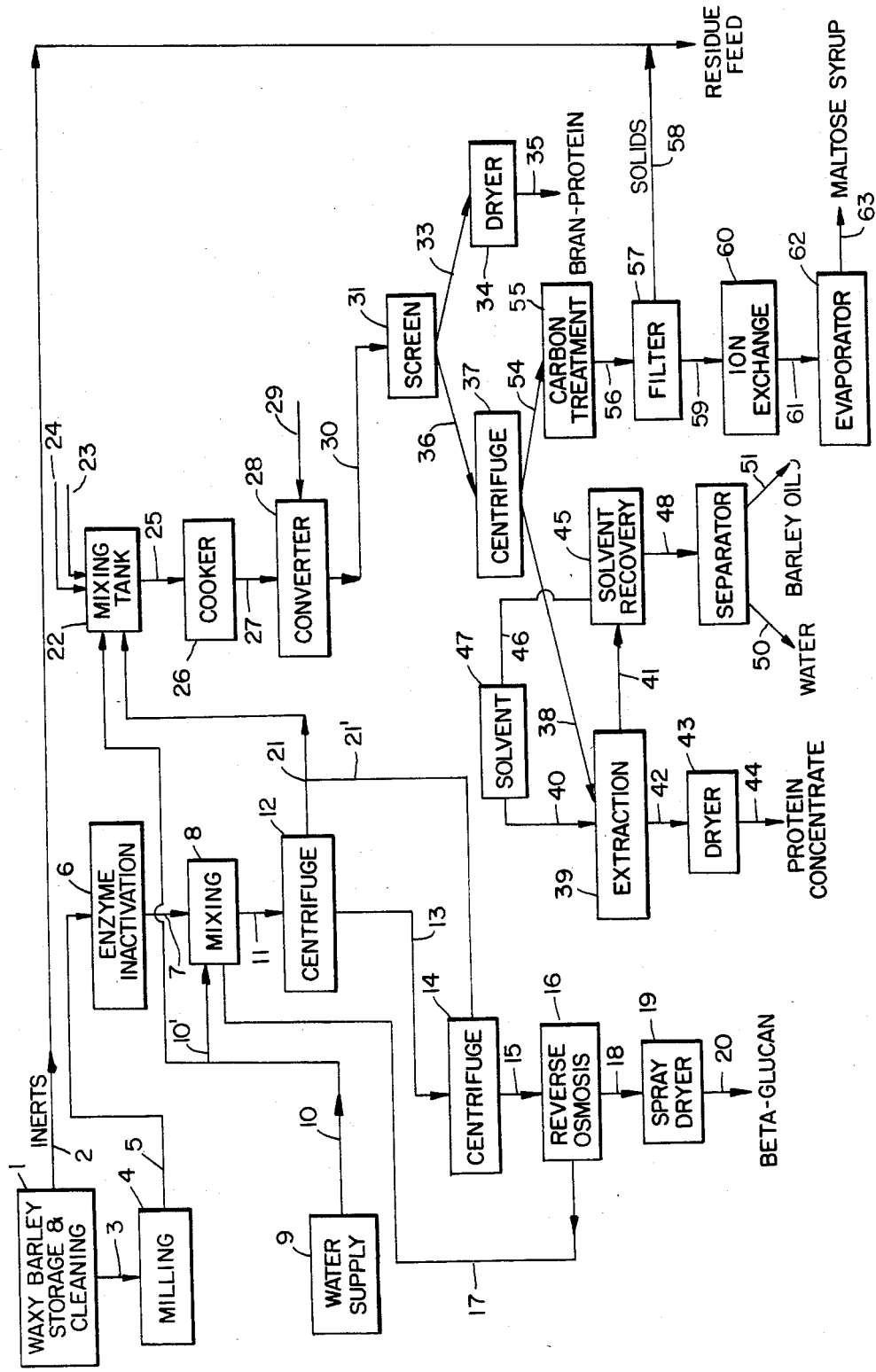

PRODUCTION OF BETA-GLUCAN, BRAN, PROTEIN, OIL AND MALTOSE SYRUP FROM WAXY BARLEY

This application is a continuation of U.S. application Ser. No. 914,877, filed on Oct. 3, 1986, now abandoned, which in turn is a continuation of U.S. application Ser. No. 639,345, filed Aug. 10, 1984, now abandoned.

FIELD OF THE INVENTION

This invention relates to the processing of waxy barley grain to obtain valuable products therefrom and more particularly, to the processing of waxy barley grain for the production of a maltose syrup, betaglucan, protein products, a barley oil and bran products.

BACKGROUND

Barley is a grain product which has been found useful mainly in the brewing industry as barley malt which utilizes the enzymatic activity of the barley malt for industrial applications such as starch-splitting and protein degrading. The barley malt is an important source of alpha- and beta-amylase and is used in many foods such as beer, wheat flour and cereal to convert starch to fermentable sugars.

There has been very limited work in the utilization of barley in other areas heretofore. Exemplary of the prior art in which there have been attempts to use barley in other ways may be found primarily in our prior U.S. Pat. Nos. 4,311,714 and 4,428,967. In these patents, novel procedures are set forth for the production and recovery of maltose syrup, protein products, barley oil, bran and a carbohydrate gum. The present application is an improvement on these prior processes.

In other art, U.S. Pat. No. 3,846,397 processes grain residues obtained from mashed barley malt to recover water soluble protein products suitable for utilization as animal feeds. U.S. Pat. No. 1,548,721 describes the treatment of starch with an ungerminated grain such as barley until the major portion of the starch has been saccharified. U.S. Pat. No. 3,689,277 discloses production of a protein hydrolysate from barley grain by treating with a proteolytic enzyme at 35°–50° C. to produce protein hydrolysis products and a starch fraction, the solution containing at least 40% of protein. The protein is then reacted with sugar to produce a product having a caramel flavor.

U.S. Pat. No. 3,901,725 describes wet processes for separating cereal starch granules according to size and states that barley, rye and wheat starch may be treated in the process. However, the patent does not set forth specific examples of obtaining any product from a barley grain. U.S. Pat. No. 4,094,700 is directed to a method for producing gluten and starch from a dispersion of wheat, barley or rye endosperm fractions in water. However, there is no actual example directed to processing of barley as the starting material or any description of a product obtained from barley.

A publication entitled "Barley Syrup Production" by the ABMIP/DDS-KROYER Process, Pamphlet No. 815G008E, published by the Danish Company, DDS-KROYER, presented in 1972 in Peking by Erik S. Nilsson, discloses a conventional procedure for processing of barley by conversion to malt through germination of the raw barley. A process is disclosed wherein an extract simulating the extract from barley malt action can be produced by degrading barley directly with enzymes such as alpha-amylase or beta-amylase.

U.S. Pat. No. 3,791,865 discloses maltose syrups obtained from corn starch wherein the syrup contains 60–80% maltose and 15–35% maltotriose.

DISCLOSURE OF THE INVENTION

It is one object of the present invention to provide a series of processing steps by which a number of valuable products can be obtained from waxy barley.

A further object of the present invention is to provide a method for processing of waxy barley grain to produce a high maltose carbohydrate syrup, protein-concentrates, a barley oil, a carbohydrate gum and bran-protein.

A still further object of the invention is to provide a complete processing system by which these products can be obtained utilizing a continuous procedure whereby the products are obtained in sufficient purity to be used in a wide spectrum of food industry products.

Other objects and advantages of the present invention will become apparent as the description thereof proceeds.

In satisfaction of the foregoing objects and advantages there is provided by this invention a manufacturing process for the recovery of valuable products from waxy barley starting materials or grain, these products comprising a barley syrup, a barley oil, a protein concentrate, beta-glucan solids, and bran protein residue. The manufacturing process comprises treatment of waxy barley grain, that is, a barley grain which contains at least about 92% amylopectin, the steps of the process broadly comprising;

(1) heating waxy barley of reduced particle size to a sufficient temperature to effect enzyme inactivation and produce an enzyme-inactivated meal;

(2) mixing said meal with water at 40°–46° C.;

(3) separating the solids and liquids;

(4) concentrating the liquids and recovering the solid beta-glucans from the liquids;

(5) removing the solids from (3), mixing with water at a temperature of about 40°–60° C. and adding at least an alpha-amylase enzyme, and preferably a beta-amylase enzyme to form a mixture;

(6) heating the mixture at a temperature of about 70°–75° C. for a sufficient time to effect starch conversion and form a starch mixture;

(7) cooling the starch mixture to a temperature of about 50°–60° C., adding at least an additional enzyme comprising beta-glucanase, and preferably an alpha-amylase enzyme, and permitting to stand at this temperature for a sufficient period to form a converted mixture;

(8) subjecting the converted mixture to a rough solids separation to produce a bran-protein residue solid and product liquid;

(9) separating the remaining solids from the liquid and extracting with an alcohol to produce a protein concentrate and recovering a barley oil from the extractant;

(10) decolorizing and deionizing the liquids to produce a maltose syrup.

BRIEF DESCRIPTION OF THE DRAWINGS

Reference is now made to the drawing accompanying the application wherein the FIGURE is a complete schematic flow sheet for a commercial processing system of the present invention.

DESCRIPTION OF PREFERRED EMBODIMENTS

The present invention is concerned with a series of processing steps by which a number of novel products are obtained from waxy barley grain which find value in various areas in industry. In particular the process provides a procedure for producing a maltose syrup, a protein concentrate, a bran-protein product, and a beta-glucan product.

The process is directed to the production of these products from waxy barleys, several strains of which are known in the art. The waxy barleys are chemically the same as starch found in waxy varieties of corn but the physical properties of the waxy barley starch are different from those of ordinary corn starch which make the barley starch easier and less expensive to process.

Several waxy barleys are described in the prior art, for example in our publications in Cereal Chemistry, 53 (2) pages 174–180, (1975), and Cereal Chemistry, 55, (2), pages 127–137, (1977), as well as our prior U.S. Pat. Nos. 4,042,414, issued Aug. 16, 1977, 4,054,671, issued Oct. 18, 1977 and 4,116,770, issued Sept. 26, 1978. These waxy barleys are produced by cross-breeding barley varieties having different genes as described in these publications. These publications and prior patents describe a barley species which is self-liquefying (Washonupana) and other waxy barleys (Wapana and Waxy Oderbrucker). The disclosures of these publications are hereby incorporated by reference, especially the disclosures which compare waxy barleys with normal barleys. Other species of waxy barleys which may be used as starting materials in the process of the invention include Watan, Wabet, Washonutan, Washonubet, Wanutan, Wanubet, and Wanupana. It should be noted that waxy barleys are usually named with the prefix "wa-", and normally contain about 98–99 wt. % of amylopectin. It should be understood that the waxy barley starting material is not limited to those named herein.

Obviously, any equivalent starting material may also be employed providing that it is a waxy type product which contains less than about 8% amylose, or alternatively, contains at least about 92% amylopectin. It should be noted that a normal barley contains about 72–80% of amylopectin and the major difference between the waxy and the normal barley is found in the amylopectin content.

The process of the present invention produces several major products from the waxy barley starting material through a series of novel processing steps. These products may be broadly described as a betaglucan product, a bran-protein product, a syrup containing in excess of 50% maltose, and generally in the range of about 52%–60% maltose by weight, a protein concentrate, and a barley oil. Alternate products can also be produced. Thus, the maltose syrup concentrate can be catalytically reduced to produce malitol which is a commercial sweetener and could be considered as an optional product to be produced from the barley in addition to those named above. With the other products, this represents a large number of potential commercial products to be recovered from the barley grain. In view of the limited use of barley heretofore, this represents an outstanding contribution to the art of processing barley grain.

Of the several products produced, the bran-protein is useful as a food supplement, particularly with current emphasis on fiber in the diet. Products low in protein content could be used as animal feeds whereas high protein containing materials such as the protein concentrate are useful in various major markets as a substitute for vital gluten which is obtained from wheat. It should be noted that the maltose syrup and the high protein products obtained from the barley according to the present invention are commercially attractive products having novel physical and chemical characteristics. Barley protein products are also useful in diets of people who may be allergic to wheat protein.

The maltose syrup in essence contains in excess of 60% maltose and less than 5% dextrose and with proper concentration, contains up to 80% solids. Thus, this type of product is highly desirable and is useful in bakery and dairy products such as cereal, sweeteners, ice cream, and brewing operations as well as hard candy products. For example, in the ice cream industry, the maltose syrup is useful in providing texture for body and crystallinity control.

These products are produced by a multi-step procedure comprising the processing of barley grain. This process if described in general in the accompanying drawing which sets forth a flow sheet for the process. The present invention represents an improvement in processing of these materials over our prior U.S. Pat. Nos. 4,311,714 and 4,428,967, referred to above. These improvements include the removal of most of the beta-glucan prior to starch conversion. This allows an extraction of the water soluble beta-glucans in substantial amounts, for example, up to 4–7% of the body weight prior to starch conversion. This results in substantially improved yields of beta-glucan so as to produce a potentially valuable byproduct and at the same time improve the syrup conversion since most of the beta-glucan is eliminated from the processing meal. With the removal of the beta-glucan, it was found that the wet milling step can be eliminated and the finely milled grain mash can be converted directly without the separation of crude starch. As a result, these two operations are eliminated, which greatly improves the efficiency of the process. This operation also eliminates the problem of processing mill water since that fraction is also eliminated.

Thus, the present invention provides a procedure by which the products produced by this invention, namely the syrup which is high in maltose content, bran protein residue, beta-glucan, 75–80% protein concentrate and barley oil, are produced by a multi-step procedure from the barley grain. As described in the flow sheet accompanying the application, the waxy barley is initially obtained from storage and cleaned to remove inert particles, dirt and the like. The inerts and other impurities may be mixed with a filter cake residue for disposal or use as desired and are removed through line 2. The grain is then removed by line 3 and milled in a conventional grinding apparatus such as a hammer mill 4. During milling, it is desirable to grind the grain to a point wherein all of the material will pass through a 45 mesh screen, but this may be varied. The resulting milled product is then passed by line 5 to a heat chamber 6, where the ground grain is heated sufficiently to inactivate the natural enzymes contained in the grain. In general, heating at this point should be in the range of about 90°–115° C. for about 1–2 hours, preferably about 100°–105° C. for about 30–60 minutes, more preferably about 105° C. for 30 minutes.

On completion of the heating step and enzyme inactivation, the resulting product is removed by line 7 to a mixing tank 8 where it is mixed with 3 to 6 parts of water, preferably about five parts of water, from source 9 through lines 10 and 10'. The water is preferably preheated so that it is at a temperature of about 40°–60° C., preferably 50° C., for mixing with the grain at this stage. The grain and water mixture should remain in the mixing tank 8 for about 5 minutes to 1 hour, preferably about 10–20 minutes, to achieve thorough mixing of the grain with the water. The tank is preferably provided with an agitator to accelerate the mixing procedure.

On completion of mixing, the resulting product is removed by line 11 to a decanter or centrifuge 12 to effect a separation between the rough solids and the liquids. The centrifuge may be any conventional device of this type which will remove most of the solids, such as a decanter centrifuge. If a decanter is used, the liquids should be subjected to a desludging step to remove sludges therefrom. Any sludges remmoved may then be mixed with the solids from the decanter. The liquids are removed from the centrifuge by line 13 to a disc centrifuge 14 or ultra centrifuge by which a more complete separation can be made. The solids from centrifuge 14 are removed by line 21 and mixed with the solids from centrifuge 12 at line 21. The liquids from the centrifuge 14 are removed by line 15 to reactor 16 wherein a reverse osmosis procedure is carried out to concentrate the solution which contains the beta-glucan solids. The water removed in the reverse osmosis apparatus is recycled by line 17 to mixing tank 8 as make up water. The concentrate from the reverse osmosis apparatus 16 are removed by line 18 for drying, preferably in spray dryer 19. The beta-glucan solids are then recovered at line 20 as a final product.

The solids from centrifuge 12 which comprise meal solids are removed by line 21 to mixing tank 22 where they are mixed with water from line 10. Sufficient water is added to obtain a mixture containing from about 20–30% dry solids. The water is also preferably maintained at a temperature of about 40°–60° C. in this portion of the process. At this point, there are preferably added two different kinds of enzyme through lines 23 and 24. One of the enzymes is a beta glucanase preparation produced by fermentation which will thin the starch and hydrolyze any beta-glucans remaining therein. there is also added an alpha-amylase containing enzyme to furnish amylases for conversion of the thin starch to sugars. The beta glucanase enzyme is preferably a commercial product sold as Cereflo, e.g. Cereflo 200L. The amylase enzyme is preferably the commercial product, Wallerstein's Malt Enzyme PF, available from the Wallerstein Company. Preferably, however, an enzyme which will provide both the alphaamylase function and beta-amylase functions is used. Green malt enzymes are preferably suitable for this purpose. Preferably, about 0.01 to 1% by weight of the enzymes are added, preferably about 0.5% of the green malt enzyme.

After addition of the enzymes, the mixing is contained in mixing tank 22 to achieve intimate association of the enzymes with the meal solids. In general, about ¼ to 1 hour is sufficient for this purpose. Thereafter, the resulting mixture is transferred by line 25 to a cooker 26 where the contents are heated in the range of 70°–75° C. and held at that point for about 1 minute to 10 minutes, preferably 1 minute to 5 minutes, to begin the starch conversion. The resulting cooked grain mash is then transferred by line 27 to converter 28 and cooled to about 55°–65° C., preferably about 60° C. and maintained at this temperature while an additional amylolytic enzyme such as the about 0.5% green malt is added through line 29. This green malt preferably has both alpha-amylase and beta-amylase activity. A betaglucanase enzyme, (e.g., about 0.0003–0.001 wt. %) may also be added at this stage to hydrolyze any beta-glucans carried over. The resulting mixture is then maintained at this temperature for about 4 to 8 hours to complete the conversion.

On completion of the starch conversion, the contents of the converter 28 are removed by line 30 to a solid or screen separator such as a Rotex Screen 31, where the solids are retained on a screen. Preferably about a 120 mesh screen is used. The solids are then removed by line 33, and dried in dryer 34. There is recovered from the dryer at line 35 a bran protein residue which is a high protein high fiber product with a pleasant flavor and is ideal as a food supplement.

In the meantime, the liquid from the screen separator 31 is recovered in line 36 and passed through centrifuge 37. Any sludges in the liquids may be removed in a desludging operation. This centrifuge is preferably a disc centrifuge or ultra centrifuge which will effect a further separation of solids and liquids to provide solids which may be removed by line 38. The solids in line 38 are then passed to an extraction device where they are mixed with a lower alkyl alcohol, preferably ethyl alcohol and more preferably, 95% ethyl alcohol from line 40. In the extractor 39, the alcohol extracts barley oil from the solids and these are removed by line 41 as a solution. The resulting solids from the extractor 39 are removed by line 42 and dried in dryer 43 to provide a protein concentrate from line 44. This protein concentrate contains about 75–80% protein.

The liquid phase in line 41 from the extractor 39 is first subjected to alcohol recovery as in distillation recovery column 45. The alcohol recovered is passed by line 46 to alcohol storage 47. The residue after removal of the alcohol is removed by line 48 to separator 49 where water is removed at 50 to provide a barley oil at 51.

The liquid from the centrifuge 37 is removed by line 54 for purification. Preferably, the liquid is initially subjected to a carbon treatment at 55 to decolorize the liquid using a conventional carbon absorption system. The resulting product is then removed by line 56 to filter 57 where any carbon particles and inert materials are removed by line 58. The filtered liquid is then transferred by line 59 and subjected to an ion exchange procedure in ion exchange column 60 to deionize the liquid and effect further purification. The resulting liquid is removed by line 61 and evaporated in a conventional evaporator 62 to produce in line 63 a maltose syrup which contains about 80% maltose solids.

It will be understood, therefore, that the invention provides methods by which the beta-glucan is removed prior to starch conversion with substantial increases in yield. This also enables the elimination of steps which are not economic.

The following examples are presented to illustrate the invention, but it is not to be considered as limited thereto. In the examples and throughout the specification, parts are by weight unless otherwise indicated.

EXAMPLE 1

This example is a pilot plant run generally using the apparatus shown in the flow sheet accompanying the application described in this specification. In this example, 15 pounds of waxy barley containing 10% moisture was milled through a hammer mill, sifted and the coarse material passed through an Allis Roller Mill until it would all pass through a 45 mesh screen. The enzymes in this meal were then inactivated by heating the meal for 8 hours at 70° C. in a circulating air oven. The meal was then mixed with 60 pounds of water, which was at 50° C., and stirred gently for 30 minutes. At this time, the contents of the mixer were then run through a Bird decanter and the beta-glucan extract was separated from the grain mash. The beta-glucan was then clarified by passing the extract through a Westfalia centrifuge which removed 50 grams of residue containing 30.8% protein. The centrifuged beta-glucan was freeze-dried and 2.3 pounds, dry weight, of betaglucan were recovered.

The meal recovered from the Bird decanter was then made up to 25% solids by the addition of water. At this point, 0.5% by weight of green malt was added and the mixture was heated up to 75° C. with continued agitation. After holding at this temperature for 5 minutes, the mixture was cooled to 60° and an additional 1.0% green malt was added. After 8 hours, the mixture was screened on a 120 mesh screen, the residue was resuspended and screened again to remove adhering sugar. This screen residue was then freeze-dried to yield 3.1 pounds on a dry basis of a bran protein residue.

The liquid passing through the screen was centrifuged in a Westfalia centrifuge, and this yielded 2.0 pounds on dry basis of crude protein. After washing out the adhering sugars, this residue weighed 1.3 pounds on a dry basis. The syrups recovered from this run were 6.2 pounds on a dry basis, which would yield 7.75 pounds of 80% solid syrup.

The following is an analysis of the products from the pilot run.

|  | % Protein | % Ash | % EE | % CF | % N.D.F. | % A.D.F. |
|---|---|---|---|---|---|---|
| Protein Bran | 15.6 | 3.1 | 4.3 | 9.2 | 36.5 | 12.2 |
| Washed Protein | 68.4 | 1.5 | 11.3 | 0.7 | 11.8 | 6.3 |
| Alcohol Extracted Protein | 78.9 | — | — | — | — | — |
| Initial Barley | 14.5 | 1.8 | 2.1 | 2.1 | 11.3 | 3.1 |

The analysis of the barley syrup was as follows:
Glucose 3.86%
Maltose 53.4%
Maltotriose & Higher 42.7%

EXAMPLE 2

This example is a pilot plant run generally using the apparatus shown in the flow sheet accompanying the specification. In this example, 568 kilograms of barley flour in 3410 liters of water was the starting mixture. After mixing was completed, the product was removed to a decanter to separate rough solids from the liquids. The liquids were removed and subjected to a desludging operation and the sludge solids recovered therefrom are mixed with the solids separated in the decanter. The remaining liquids are then subjected to evaporation using a reverse osmosis apparatus and the resulting concentrate is spray-dried resulting in the recovery of 50 kilograms of beta-glucan solids.

The solids from the decanter are then removed to the starch conversion process with sufficient water being added to provide a 33% solid solution. To this solution is added 5 kilograms of green malt and 220 mililiters of Cereflow 200 L. The mixture is heated to 70° C. for five hours and then cooled to 60° C. and an additional 5 kilograms of green malt were added. The mixture was then held overnight and screened on a 120 mesh Rotex screen. The solid recovered was a bran protein which, on washing and drying yielded 121.3 kilograms of bran protein.

The liquid from the screen separation step was subjected to desludging, the solids were removed, washed and extracted with ethyl alcohol, and dried to provide 43 kilograms of protein concentrate. The liquid syrup was decolorized and evaporated to yield 380 kilograms of maltose syrup.

Thus, from this pilot plant experiment was recovered 50 kilograms of beta-glucan solids, 121.3 kilograms of bran protein, 43 kilograms of protein concentrate, and 380 kilograms of maltose syrup, some of the syrup being lost in the filtering step. The analyses of the products on a weight basis are as follows, this analysis being an average compilation for four runs:
Glucose: 2.6%
Maltose: 52.2%
Maltotriose: 10.0%
Higher: 35.2%

The analysis of the bran protein and protein concentrate was as follows:

|  | % Protein | % Ash | % Crude Fiber | % EE | % NDF |
|---|---|---|---|---|---|
| Bran Protein | 27.4 | 1.72 | 13.8 | 5.2 | 57.8 |
| Protein Concentrate | 74.4 | 0.47 | 5.4 | 1.75 | — |

It was noted that in this experiment, the bran protein concentration was much higher than normal runs. However, this was believed to be caused by use of a barley variety called Westbred, which is very high in NDF, but this makes it a valuable additive to foods because of the demand for high fiber food products.

The protein concentrate had a protein level somewhat lower than expected, and a higher fat content. A finer screen on the Rotex screening apparatus may be useful to adjust the protein level.

The invention has been described herein with reference to certain preferred embodiments. However, as obvious variations thereof will become apparent to those skilled in the art, the invention is not to be considered as limited thereto.

What is claimed is:

1. A method for the production and recovery of beta-glucan solids, bran residue, a protein concentrate, barley oil and maltose syrup from waxy barley which comprises the steps of:

(1) reducing the particle size of the waxy barley to form a meal, heating the meal at a temperature of about 90°–115° C. for a sufficient period to effect inactivation of natural enzymes in the meal to form an enzyme-inactivated meal, extracting beta-glucan solids from the enzyme-inactivated meal by mixing the meal solely with water at a temperature of about 40°–60° C., to produce a water extract and barley solids, and recovering the beta-glucan solids from the water extract;

(2) recovering the barley solids, mixing with water, and adding an amylolytic enzyme and a beta-glucanase enzyme, heating at a temperature of about 70°–75° C. for a sufficient period to effect starch conversion;

(3) cooling the mixture to about 50°–60° C. and adding an enzyme which has at least alpha-amylase activity and maintaining the mixture at this temperature to complete starch conversion and form a starch mixture;

(4) separating rough solids from this starch mixture and recovering a bran residue rough solids;

(5) subjecting the remaining starch mixture to additional separation to separate solids from the liquid, extracting the solids with an alcohol to recover a protein concentrate and an extracted barley oil;

(6) recovering the barley oil and protein concentrate; and (7) recovering maltose syrup from the liquid of step (5).

2. A method according to claim 1 wherein the enzyme added in step (3) comprises both alpha-amylase enzyme and beta-amylase enzyme.

3. A method according to claim 2, wherein the enzyme is a green malt enzyme which has both alpha-amylase and beta-amylase activity.

4. A method according to claim 1 wherein the meal in step (1) is heated at the temperature of about 90°–115° C. for about 1 to 2 hours.

5. A method according to claim 1 wherein the water extract containing the beta-glucans is subjected to reverse osmosis to remove and recover concentrated beta-glucans.

6. A method according to claim 2 wherein about 0.5% by weight of enzyme solids are added to the starch conversion mixture.

7. A method according to claim 1 wherein step (2) is carried out by heating the barley solids at a temperature of about 70°–75° C. for about 1 minute to 10 minutes, then cooled to a temperature of about 55°–65° C., the amylolytic enzyme and beta-glucanase enzyme are added and the mixture is maintained in a static condition for about 4–8 hours to effect starch conversion and form a starch conversion mixture.

8. A method according to claim 1 wherein the alcohol in step (5) is ethyl alcohol which is then recovered and recycled for additional extraction.

9. A method according to claim 1 wherein the protein concentrate is dried to form a protein concentrate containing 75–80% protein.

10. A method according to claim 1 wherein in step (7) the maltose syrup is recovered from the liquid by decolorization of the liquid with carbon, filtration of carbon particles and insert materials from the liquid, deionization of the liquid by ion exchange and evaporation of the liquid to produce an 80% solids maltose syrup.

11. A method according to claim 1 wherein the inactivation of natural enzymes in step (1) is carried out by heating at a temperature of about 105° C. for about 30 minutes.

12. A method for the production and recovery of beta-glucan, protein concentrate, barley oil, and maltose syrup from waxy barley which comprises the steps of:

(1) heating waxy barley of reduced particle size to a temperature of about 90°–115° C. for about 1 to 2 hours to effect inactivation of natural enzymes and produce an enzyme-inactivated meal;

(2) mixing said meal solely with water at a temperature of about 40°–60° C. to form a slurry containing liquid and meal solids;

(3) separating from the meal solids from the liquid;

(4) concentrating the liquid and recovering solid beta-glucans therefrom;

(5) removing the meal solids from (3), mixing with water at 40°–60° C. and adding alpha-amylase enzyme and beta-glucanase enzyme to form a mixture;

(6) heating the mixture at a temperature of 70°–75° C. for starch conversion, to form a starch mixture;

(7) cooling the starch mixture to about 50°–60° C., adding additional enzyme which contains alpha-amylase and beta-amylase, and completing starch conversion to produce a converted mixture;

(8) subjecting the converted mixture to a rough solids separation to produce a bran residue solid and product liquid;

(9) separating the bran residue solid from the product liquid, extracting a barley oil from the solid and drying the solid to form a protein concentrate; and

(10) purifying the product liquid to produce a maltose syrup.

13. A method according to claim 12 wherein the beta-glucans in step (4) are recovered by reverse osmosis to remove the beta-glucans which are then dried and recovered.

14. A method according to claim 12 wherein about 0.5 wt. % of a green malt containing alpha and beta-amylase enzymes is added to the starch conversion mixture in step (7).

15. A method according to claim 12 wherein the mixture in step (6) is heated at the temperature of about 70°–75° C. for about 1 minute to 10 minutes.

16. A method according to claim 12 wherein the solids from step (9) which are not extracted are then dried to form a protein concentrate containing 75–80% protein.

17. A method according to claim 12 wherein the liquid in step (10) is purified by decolorization with carbon, filtration of carbon particles and inert materials from the liquid, deionization of the liquid by ion exchange and evaporation of the liquid to produce an 80% solids maltose syrup.

* * * * *